United States Patent [19]

Tsuboniwa et al.

[11] Patent Number: 5,070,167
[45] Date of Patent: Dec. 3, 1991

[54] NOVEL PEROXIDE MONOMER AND A POLYMER THEREFROM

[75] Inventors: Noriyuki Tsuboniwa, Higashiosaka; Satoshi Urano; Ryuzo Mizuguchi, both of Yawata, all of Japan

[73] Assignee: Nippon Paint Co., Ltd., Osaka, Japan

[21] Appl. No.: 661,622

[22] Filed: Feb. 28, 1991

Related U.S. Application Data

[62] Division of Ser. No. 201,964, Jun. 3, 1988.

[30] Foreign Application Priority Data

Jun. 4, 1987 [JP] Japan .................................. 62-142092
Jun. 4, 1987 [JP] Japan .................................. 62-142093

[51] Int. Cl.$^5$ .............................................. C08F 8/06
[52] U.S. Cl. .................................. 526/301; 525/328.2; 525/387
[58] Field of Search ....................... 526/301; 525/328.2

[56] References Cited

U.S. PATENT DOCUMENTS 3,853,937 12/1974 Naarmann ........................... 526/310

FOREIGN PATENT DOCUMENTS 1184618 3/1970 United Kingdom .

*Primary Examiner*—Bernard Lipman
*Attorney, Agent, or Firm*—Wenderoth, Lind & Ponack

[57] ABSTRACT

Disclosed is a peroxide monomer having the formula:

$$CH_2=CR-A-OO-B \qquad (I)$$

wherein R represents a hydrogen atom or an alkyl having 1 to 5 carbon atoms, A represents —NH—CO—, —CO—NH—CO—, or —CO—O—CH$_2$CH$_2$—NH—CO—, and B represents a moiety which has excluded the group (—OOH) from a hydroperoxide and a preparation thereof. The present invention also provides a polymer whose a main chain composed of carbon-carbon bonds is bonded with a pendant peroxide group represented by the formula:

$$-A-OO-B \qquad (II)$$

wherein A and B is the same as mentioned above, the content of the pendant peroxide group being 0.1 to 99.9% by weight and a molecular weight of said polymer being 1,000 to 100,000; and a preparation thereof.

2 Claims, No Drawings

NOVEL PEROXIDE MONOMER AND A POLYMER THEREFROM

This is a divisional of U.S. application Ser. No. 07/201,964, filed June 3, 1988.

FIELD OF THE INVENTION

The present invention relates to a novel peroxide having a polymerizable double bond and a polymer therefrom.

BACKGROUND OF THE INVENTION

There is known a compound which has both a polymerizable double bond and a peroxide group in one molecule, i.e. allylperoxy carbonate of the formula;

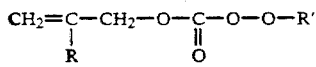

wherein R' represents an alkyl group and a cycloalkyl group and R represents a hydrogen atom and an alkyl group. However, a portion containing a double bond is an allyl group which is poor in homo- and co-polymerizability.

It is, therefore, desired to provide a novel peroxide having a polymerizable double bond.

SUMMARY OF THE INVENTION

The present invention provides a peroxide monomer having the formula;

$$CH_2=CR-A-OO-B \qquad (I)$$

wherein R represents a hydrogen atom or an alkyl having 1 to 5 carbon atoms, A represents —NH—CO—, —CO—NH—CO—, or —CO—O—CH$_2$CH$_2$—NH—CO—, and B represents a moiety which has excluded the group (—OOH) from a hydroperoxide, and a preparation thereof.

The present invention also provides a polymer whose main chain composed of carbon-carbon bonds is bonded with a pendant peroxide group represented by the formula;

$$-A-OO-B \qquad (II)$$

wherein A and B is the same as mentioned above, the content of the pendant peroxide group being 0.1 to 99.9 % by weight and a molecular weight of said polymer being 1,000 to 100,000; and a preparation thereof.

DETAILED DESCRIPTION OF THE INVENTION

The peroxide monomer can be prepared by reacting a hydroperoxide with an isocyanate compound of the formula;

$$CH_2=CR-NCO \qquad (III)$$

$$CH_2=CR-CO-NCO \qquad (IV)$$

$$CH_2=CR-CO-O-CH_2CH_2-NCO \qquad (V)$$

wherein R is the same as mentioned above.

The isocyanate compounds (III) to (V) are known. The compound (III) may be prepared by, for example, a process described in Angrew. Chem. Int. Ed. Engl. 18(1979) No.4. The compound (IV) may be prepared by a process disclosed in Japanese Patent Publication (unexamined) 115557/1985, or a process from an intermediate shown in Die Makromoleklare Chemie, 131, (1970), 247-257 (No.3199). Also, United Kingdom Patent 1,252,099 discloses one process for preparing the isocyanate compound (V).

The hydroperoxide employed in the reaction is a hydrogen peroxide of which one hydrogen is substituted for an alkyl group or another organic atom group. Examples of the hydroperoxides are t-butyl hydroperoxide, cumene hydroperoxide, diisopropylbenzene hydroperoxide, p-mentane hydroperoxide, peracetic acid, 2,5-dimethyl-2,5-dihydroperoxyhexane, 2,5-dimethyl-2,5-dihydroperoxyhexane-3 and the like. The hydroperoxide can be available in the form of a concentrated or diluted solution. If it is obtained in the form of an aqueous solution, water may be substituted for an organic solvent by, for example, extraction. Also, the aqueous hydroperoxide solution may be employed intact, but an undesired by-product, such as an amide, may be produced.

A reaction of the isocyanate compound with the hydroperoxide can be carried out in an inert solvent, if desired. The inert solvent is one that does not adversely affect on the reaction per se, including an aliphatic hydrocarbon, such as pentane, hexane, heptane and the like; an aromatic hydrocarbon, such as benzene, toluene, xylene and the like; a cyclohydrocarbon, such as cyclohexane, methylcyclohexane, decaline, and the like; a hydrocarbon type solvent, such as petroleum ether, petroleum benzine and the like; a halogenated hydrocarbon, such as carbon tetrachloride, chloroform, 1,2-dichloroethane and the like; an ether, such as ethyl ether, isopropyl ether, anisol, dioxane, tetrahydrofuran, and the like; a ketone, such as acetone, methyl ethyl ketone, methyl isobutyl ketone, cyclohexanone, acetophenone, isophorone and the like; an ester, such as ethyl acetate, butyl acetate and the like; acetonitrile; dimethylformamide; dimethylsulfoxide; and the like. The reaction can be carried out at a temperature at which the hydroperoxide is not decomposed, for example −20° to 10° C. If a temperature is over 10° C., the hydroperoxide would have a risk to decompose. If a temperature is too low, its reaction rate decreases. A catalyst may be used in the reaction, but generally no catalyst is needed in this reaction.

If necessary, a polymerization inhibitor may be added in the reaction system to prevent unnecessary polymerization on terminal double bonds. Examples of the polymerization inhibitors are hydroquinone, p-methoxyphenol, 2,6-di-t-butyl-4-methylphenol, 4-t-butylcatechol, bisdihydroxybenzylbenzene, 2,2'-methylenebis(6-t-butyl-3-methylphenol), 4,4'-butylidene(6-t-butyl-3-methylphenol), 4,4'-thiobis(6-t-butyl-3-methylphenol), p-nitrosophenol, diisopropylxantogensulfide, N-nitrosophenylhydroxylamine ammonium salt, 1,1-diphenyl-2-picrylhydrazine, 1,3,5-triphenylpheldazyl, 2,6-di-t-butyl-alpha-(3,5-di-butyl-4-oxo-2,5-cyclohexadiene-1-ilydene)-p-trioxy, 2,2,6,6-tetramethyl-4-piperidone-1-oxy, dithiobenzoylsulfide, p,p'-ditolyltrisulfide, p,p'-ditolyltetrasulfide, dibenzyltetrasulfide, tetraethylthiuramsulfide and the like.

The reaction can be carried out by adding the hydroperoxide to the isocyanate compound (III-IV), vice versa. Termination of the reaction can be identified by disappearance of an absorption of isocyanate groups in infrared spectrum.

The obtained peroxide monomer can be isolated, but can be employed intact. The obtained peroxide monomer has the following structure;

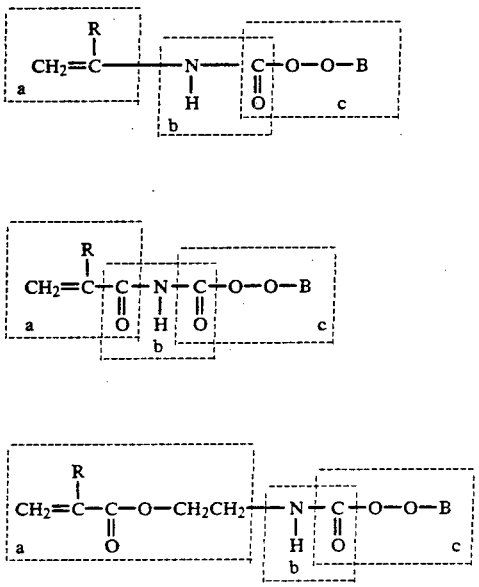

The portion a of the above chemical structure shows a double bond which is incorporated into a polymer backbone to form a polymer having a pendant peroxide group. The portion b produces

after decomposing the portion c by heat and decarboxylation, and is reacted with another functional group to be able to form a graft resin. The portion c is radically decomposed by heat to act as an initiator. Accordingly, the peroxide monomer of the present invention acts as a radical initiator and then form itself a polymer chain as a monomer.

The pendant peroxide group-containing polymer of the present invention can be prepared by two processes. The first process is that the peroxide monomer obtained in the present invention is polymerized alone or copolymerized with another polymerizable monomer. The second one is that the isocyanate monomer (III), (IV) or (V) is polymerized alone or copolymerized with another monomer to obtain a polymer having isocyante groups which are then reacted with the hydroperoxide.

The first process will be explained. In copolymerization, a monomer to be copolymerized with the peroxide monomer can be classified for convenience into an active hydrogen containing-ethylenically unsaturated compound and an ethylenically unsaturated compound not containing an active hydrogen. Examples of the active hydrogen containing-ethylenically unsaturated compounds are unsaturated acids, such as acrylic acid, methacrylic acid, crotonic acid, cinnamic acid, 2-isopropylacrylic acid, trans (cis)-2-decenoic acid, alpha-chloroacrylic acid, beta-transnitroacrylic acid and the like; unsaturated alcohols, such as crotonic alcohol, cinnamyl alcohol, o-hydroxystyrene, an monoester of a glycol (such as ethylene glycol, propylene glycol) and the above mentioned unsaturated acid, and the like; unsaturated amides, such as amides of the above listed unsaturated acids, for example acrylamide, methacrylamide, crotonamide, cinnamamide, p-benzamidestyrene and the like; unsaturated sulfonic acids and a salt thereof, such as 2-sulfoethyl acrylate, 2-sulfoethyl methacrylate, t-butylacrylamide sulfonic acid, 4-sulfophenyl acrylate, p-vinylbenzene sulfonic acid, and the like; unsaturated phosphoric acid, for example acid phosphooxyethylmethacrylate, 3-chloro-2-amidephosphooxypropyl methacrylate, acid phosphooxypropyl methacrylate, vinyl phosphate, isopropenyl phosphate and the like; unsaturate amines, such as allylamine, o-aminostyrene, m-aminostyrene, t-butylaminoethyl methacrylate, 7-amino-3,7-dimethyloctyl acrylate and the like. These are employed alone or in combination.

Examples of the ethylenically unsaturated compounds not having an active hydrogen are monoolefin and diolefin hydrocarbons, such as styrene, alpha-methylstyrene, ethylene, propylene, butylene, amylene, xylene, butadiene-1,3, isoprene and the like; halogenated monoolefin and diolefin hydrocarbons, such as alpha-chlorostyrene, 2,5-dibromostyrene, 3,4-dichlorostyrene, o-, m- and p-fluorostyrene, 2,6-dichlorostyrene, 3-fluoro-4-chlorostyrene, 3-chloro-4-fluorostyrene, 2,4,5-trichlorostyrene, 2-chlorohexene, 2-bromoheptene, 2-iodopentene, cis- and trans-1,2-dichloroethylene, 1,2-dibromoethylene, 1,2-difluoroethylene, 1,2-diiodoethylene, chloroethylene(vinyl chloride), 1,1-dichloroethylene(vinylidene chloride), 1,1-dibromoethylene, 1,1,2-trifluoroethylene, chlorobutadiene and other halogenated diolefin compounds; organic and inorganic esters, such as vinyl acetate, vinyl butylate, vinyl isobutylate, vinyl valerate, vinyl benzoate, vinyl halobenzoate, vinyl-p-methoxybenzoate, methyl (meth)acrylate, ethyl (meth)acrylate, propyl (meth)acrylate, butyl (meth)acrylate, amyl (meth)acrylate, hexyl (meth)acrylate, methyl crotonate and ethyl tiglate, isopropenyl acetate, isopropenyl butylate, isopropenyl valerate, isopropenyl caproate, isopropenyl benzoate, isopropenyl-p-chlorobenzoate, vinyl-alpha-chloroacetate, vinyl-alpha-bromovalerate and the like; esters derived from alkenyl alcohols, such as allyl chloride, allyl cyanide, allyl chloride carbonate, allyl nitrate, allyl thiocyanate, allyl formate, allyl acetate, acetate propionate, allyl butylate, allyl crotonate, allyl aminoacetate, allyl acetoacetate, allyl thioacetate, beta-ethylallyl alcohol, beta-propylallyl alcohol and the like; organic nitriles, such as acrylonitrile, methacrylonitrile, ethacrylonitrile, 3-octenenitrile, crotonitrile, oleonitrile and the like.

Polymerization or copolymerization is generally carried out in the presence of a polymerization initiator in a solvent which is inactive with the polymerization. The polymerization initiator is preferably a radical initiator, such as azobisisobutylonitrile, bezoyl peroxide, cumene peroxide, tetramethylthiuram disulfide, 2,2'-azobis(4-methoxy-2,4-dimethylvaleronitrile), acetylcyclohexylsulfonyl peroxide, 2,2-azobis(2,4-dimethylvaleronitrile) and the like. The polymerization initiator can be used in an amount of 0.1 to 10% by weight based on a monomer weight. Examples of the solvents are the above mentioned inert solvents, alcohols or a mixture thereof. Polymerization may be carried out at a temperature of 40° to 150° C., preferably 40° to 80° C.

In the second process, since the isocyanate compound is used uncapped or unblocked, a compound reactive with an isocyanate group can not be employed in the polymerization reaction and the reaction with the hydroperoxide. Accordingly, a solvent which contains an active hydrogen can not be employed and a monomer which contains an active hydrogen also can not be used.

The reaction of the polymer in the sencond process with the hydroperoxide may be conducted with equal molar ratio so that all isocyanate groups are consumed for the hydroperoxide. Also, the hydroperoxide may be used in a less molar amount than the isocyanate groups to leave a part of the isocyanate groups for further reactions. The remained isocyanate groups may be reacted with other active hydrogen containing-compounds, whereby other functional groups can be incorporated into the polymer. Examples of the other active hydrogen containing-compounds are alcohols, phenols, active methylenes, lactams, N-hydroxyimides, oximes, imidazols, triazoles and amines. Also, a fluorine-containing compound, a melamine derivative, a spiro compound, an Si group containing compound, a glycidol, a photocrosslinkable compound or a ultraviolet absorbent may be reacted to be coexistent with the peroxide groups. It may also be reacted with an active hydrogen containing ethylenically unsaturated compound to introduce polymerizable double bonds.

The polymer of the present invention schemetically shows as follow.

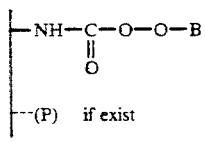

It is understandable from the above chemical structure that the polymer of the present invention has a radical initiating ability at a portion which has been decomposed by heat to form a graft polymer. In the structure, P shows the other pendant groups. If P is an ethylenically unsaturated group, the polymer has both an unsaturated group and a peroxide group so as to be able to cure without externally adding a curing agent.

In the first process for preparing the polymer, an isocyanate group is already blocked so as to freely select a solvent or another monomer. Also, it is not needed to consider gelation with water during polymerizing.

In the second process, it is not necessary to take care to a decomposing temperature of the peroxide, so that a conventional radical polymerization can be employed. There also would be few decomposing loss of the hydroperoxide.

EXAMPLES

The present invention is illustrated by the following examples which, however, are not to be construed as limiting the scope of the present invention to their details.

EXAMPLE 1

An adduct of methacryloyl isocyanate and cumene hydroperoxide

Methacryloyl isocyanate (1.10 g; 10 mmol) and dichloroethane (20 g) were mixed and cooled to 0° to 2° C. A mixture of a 73% cumene hydroperoxide solution in a hydrocarbon (21.0 g; 10 mmol) with dichloroethane (20 g) was added dropwise for about 5 minutes and mixing was continued for one hour. After it was identified that an absorption of NCO by infrared spectrum disappeared, a small amount of solvent was removed by an evaporator to obtain a 5% product solution in dichloroethane which has a viscosity Cp of 1.5 (25° C., EL type viscometer).

EXAMPLE 2

An adduct of methacryloyl isocyanate and t-butyl hydroperoxide

Methacryloyl isocyanate (1.42 g; 12.8 mmol) was dissolved in dichloroethane (5 g) and cooled to 0° C. A 14% dichloroethane solution (8.2 g; 12.8 mmol) of t-butyl hydroperoxide was added dropwise for about 30 minutes and mixing was continued for about one hour. The 14% dichloroethane solution of t-butyl hydroperoxide was prepared by extracting an 80% t-butyl hydroperoxide aqueous solution with dichloroethane and then drying with magnesium sulfate followed by identifying a content by NMR. After it was identified that an absorption of NCO by infrared spectrum disappeared, dichloroethane was removed at a low temperature by an evaporator and dried by a vacuum pump to obtain white solid having a melting point of 55° to 60° C. and a decomposing point of 115° to 120° C.

EXAMPLE 3

An adduct of isocyanatoethyl methacrylate and t-butyl hydroperoxide

Isocyanatoethyl methacrylate (1.55 g; 10 mmol) was dissolved in dichloroethane (5 g) and cooled to 0° C. A 18% dichloroethane solution (9.0 g; 10 mmol) of t-butyl hydroperoxide was added dropwise for about 10 minutes. Triethylamine (20 mg; 2 mol %) was then added and mixing was continued for about one hour. After it was identified that an absorption of NCO by infrared spectrum disappeared, it was concentrated under a reduced pressure by a vacuum pump to obtain an oil product having a viscosity (Cp) of 127.6 (25° C., EL type viscometer).

EXAMPLE 4

A copolymer having an acylisocyanate blocked by t-butyl hydroperoxide

Methacryloylisocyanate (2.2 g; 20 mmol) and butyl acetate (2.0 g) were cooled to 15° to 20° C. and a 20% toluene solution (6.0 g; 20 mmol) of t-butyl hydroperoxide was added dropwise for 5 minutes. The toluene solution of t-butyl hydroperoxide was prepared by extracting several times an 80% t-butyl hydroperoxide aqueous solution with toluene and then drying with magnesium sulfate followed by identifying a content by NMR. After it was identified that an absorption of NCO by infrared spectrum disappeared and that an absorption of the adduct exists at 1,800 cm$^{-1}$, n-butyl acrylate (4.4 g) and methyl methacrylate (2.0 g) were added and mixed at 80° C. Next, 2,2'-azobis(2,4-dimethyl)valeronitrile (available from Wako pure Chemical Industries, LTD. as V-65) (3%; 300 mg) was dissolved in butyl acetate (5.0 g), which was added to the mixture obtained above for about 30 minutes. It was aged for one hour to obtain a copolymer having a number average molecular weight of 1,590 and a conversion of 61%.

EXAMPLE 5

A copolymer having a pendant acylisocyanate blocked by t-butyl hydroperoxide

Methacryloyl isocyanate (1.7 g; 15 mmol), n-butyl acrylate (4.0 g), styrene (2.0 g) and 2,2'-azobis(2,4-dimethyl)valelonitrile (V-65) (231 mg; 3%) were mixed and added dropwise to butyl acetate (10.0 g) at 110° C. for one hour. At 110° C., the resultant mixture was aged for 2 hours and cooled to 0° to 5° C., to which a mixture of a 50% benzene solution (2.7 g) of t-butyl hydroperoxide with butyl acetate (4.2 g) was added dropwise for 10 minutes and continued to mix. The benzene solution of t-butyl hydroperoxide was prepared by extracting several times a t-butyl hydroperoxide aqueous solution with benzene and then drying with magnesium sulfate followed by identifying a content by NMR. It was identified that an absorption of NCO by infrared spectrum disappeared. An objective resin was obtained with a conversion of 80% and a number average molecular weight of 6,300.

EXAMPLE 6

A copolymer having a pendant acylisocyanate blocked by cumene hydroperoxide

Methacryloyl isocyanate (2.8 g; 25 mmol), n-butyl acrylate (8.0 g), styrene (4.0 g) and 2,2'-azobis(2,4-dimethyl)valelonitrile (V-65) (444 mg; 3%) were mixed and added dropwise to butyl acetate (15.0 g) at 110° C. for one hour. At 110° C., the resultant mixture was aged for 2 hours and cooled to 0° to 5° C., to which a mixture of a 73% cumene hydroperoxide solution (5.2 g) with butyl acetate (1.0 g) was added dropwise for about 5 minutes and continued to mix for one hour. It was identified that an absorption of NCO by infrared spectrum disappeared. An objective resin was obtained with a conversion of 80% and a number average molecular weight of 7,200.

EXAMPLE 7

A copolymer having a pendant isocyanate blocked by t-butyl hydroperoxide

Isocyanatoethyl methacrylate (1.6 g; 10 mmol), butyl acrylate (4.0 g), styrene (1.5 g) and 2,2'-azobis(2,4-dimethyl)valelonitrile (V-65) (220 mg; 3%) were mixed and added dropwise to butyl acetate (11.3 g) at 100° C. for one hour. At 100° C., the resultant mixture was aged for one hour and cooled to 0° C., to which a mixture of a 50% benzene solution (1.8 g; 10.0 mmol) of t-butyl hydroperoxide with butyl acetate (4.5 g) was added dropwise for 30 minutes and continued to mix. Then, dibutyltin dilaulate (20 mg) was added and mixed at room temperature for one day. It was identified that an absorption of NCO by infrared spectrum disappeared. An objective resin was obtained with a conversion of 78% and a number average molecular weight of 7,700.

EXAMPLE 8

A copolymer having a pendant acylisocyanate blocked by t-butyl hydroperoxide and a double bond Methacryloyl isocyanate (3.1 g; 28 mmol), n-butyl acrylate (4.7 g), methyl acrylate (3.4 g) and 2,2'-azobis(2,4-dimethyl)valelonitrile (V-65) (300 mg; 3%) were mixed and added dropwise to butyl acetate (17.0 g) at 85° C. for one hour. The resultant mixture was aged for one hour and cooled to 10° C., to which a mixture of 2-hydroxyethyl methacrylate (2.0 g; 15.6 mmol) with butyl acetate (1.0 g) was added dropwise. Next, (8.0 g; 12.4 mmol) of a dichloroethane solution containing t-butyl hydroperoxide at an concentration of 14% was diluted with butyl acetate (16 g) and added dropwise. The dichloroethane solution of t-butyl hydroperoxide was prepared by extracting several times a t-butyl hydroperoxide aqueous solution with dichloroethane and then drying with magnesium sulfate followed by identifying a content by NMR. It was identified that an absorption of NCO by infrared spectrum disappeared. An objective resin was obtained with a conversion of 75% and a number average molecular weight of 8,800.

EXAMPLE 9

A copolymer having acylisocyanates, a part of which is blocked by t-butyl hydroperoxide and the other part of which is blocked by phenol Methacryloyl isocyanate (3.1 g; 28 mmol), n-butyl acrylate (4.7 g), methyl methacrylate (3.4 g) and 2,2'-azobis(2,4-dimethyl)valelonitrile (V-65) (300 mg; 3%) were mixed and added dropwise to butyl acetate (17.0 g) at 85° C. for one hour. At 85° C., the resultant mixture was aged for 1 hours and cooled to 10° C., to which a mixture of phenol (1.47 g; 15.6 mmol) with butyl acetate (1 g) was added dropwise. Then, it was aged for one hour and a mixture of a 14% dichloroethane solution (8.0 g; 12.4 mmol) of t-butyl hydroperoxide with butyl acetate (16 g) was added dropwise. The dichloroethane solution of t-butyl hydroperoxide was prepared by extracting several times a t-butyl hydroperoxide aqueous solution with dichloroethane and then drying with magnesium sulfate followed by identifying a content by NMR. After completion of addition, mixing was continued for 30 minutes. It was identified that an absorption of NCO by infrared spectrum disappeared. An objective resin was obtained with a conversion of 70% and a number average molecular weight of 8,500.

Hexane was added to each copolymer obtained in Examples 1 to 4 and 6 to take a solid portion which was washed several times with hexane to obtain a sample. The sample was mixed with ethylene glycol dimethacrylate and n-butyl acrylate and heated to 120° C. to observe gelation due to radical polymerization.

Hexane was added to the copolymer of Example 5 to take out a solid portion which was then washed several times with hexane to obtain a sample. The sample was dissolved in butyl acetate and heated to 120° C. to observe gelation due to radical polymerization.

What is claimed is:

1. A polymer, whose main chain composed of carbon-carbon bonds, is bonded with a pendant peroxide group represented by the formula;

—A—OO—B    (II)

wherein A represents —NH—CO—, —CO—NH—CO—, or —CO—O—CH$_2$CH$_2$—NH—CO—, and B represents a moiety which has excluded the group (—OOH) from a hydroperoxide, the content of the pendant peroxide group being 0.1 to 99.9% by weight and the molecular weight of said polymer being 1,000 to 100,000.

2. The polymer according to claim 1 wherein the polymer further contains a polymerizable double bond.

* * * * *